(12) United States Patent
Corazzari (10) Patent No.: US 10,335,246 B2
(45) Date of Patent: Jul. 2, 2019

(54) DISPOSABLE KIT FOR MEDICAL APPARATUS

(71) Applicant: B. BRAUN AVITUM AG, Melsungen (DE)

(72) Inventor: Enrico Corazzari, Modena (IT)

(73) Assignee: B. Braun Avitum AG (DE)

( * ) Notice: Subject to any disclaimer, the term of this patent is extended or adjusted under 35 U.S.C. 154(b) by 19 days.

(21) Appl. No.: 15/475,262

(22) Filed: Mar. 31, 2017

(65) Prior Publication Data

US 2017/0296286 A1    Oct. 19, 2017

(30) Foreign Application Priority Data

Apr. 15, 2016   (EP) .................................... 16165578

(51) Int. Cl.
| | |
|---|---|
| *A61B 50/33* | (2016.01) |
| *A61B 50/20* | (2016.01) |
| *B65D 25/10* | (2006.01) |
| *A61M 1/34* | (2006.01) |
| *A61M 1/36* | (2006.01) |

(52) U.S. Cl.
CPC .............. *A61B 50/33* (2016.02); *A61B 50/20* (2016.02); *A61M 1/34* (2013.01); *A61M 1/367* (2013.01); *A61M 1/3627* (2013.01); *B65D 25/10* (2013.01); *A61M 2205/125* (2013.01); *A61M 2209/06* (2013.01)

(58) Field of Classification Search
USPC ....................................................... 206/370
See application file for complete search history.

(56) References Cited

U.S. PATENT DOCUMENTS 5,350,357 A * 9/1994 Kamen ................... A61M 1/28
                                                                604/29
5,779,053 A * 7/1998 Partika ................... A61B 50/33
                                                                206/370

(Continued)

FOREIGN PATENT DOCUMENTS

| EP | 1413527 A1 | 4/2004 |
| JP | 2010200886 A | 9/2010 |
| WO | 2009146912 A2 | 12/2009 |

OTHER PUBLICATIONS

European Search Report for Application No. EP 16165578.2, dated Oct. 10, 2016, 9 pages.

*Primary Examiner* — Jacob K Ackun
(74) *Attorney, Agent, or Firm* — RatnerPrestia (57) ABSTRACT

A disposable kit for a medical apparatus includes a tray and a subassembly with sections foldably connected to each other. At least one of the sections can fold itself onto the tray so that the subassembly encloses a region of the tray. When the tray is laid on the subassembly in a predetermined position, elevated channel regions formed on a front side of the tray and facing the subassembly can accommodate component installations of the subassembly, and a section of the subassembly can be folded to the rear side of the tray so that component installations on that section can be accommodated in elevated channel regions formed on the rear side of the tray. In this manner, the subassembly forms a hard-shell that at least partially surrounds the tray and protects pre-installed or packed pressure-sensitive components, parts and or regions of the disposable kit.

13 Claims, 8 Drawing Sheets

(56) References Cited

U.S. PATENT DOCUMENTS

| | | | | |
|---|---|---|---|---|
| 5,906,598 A * | 5/1999 | Giesler | ............... | A61M 5/1411 |
| | | | | 206/564 |
| 5,947,284 A * | 9/1999 | Foster | ................... | A61B 50/33 |
| | | | | 206/364 |
| 6,311,838 B1 * | 11/2001 | Johnson | ................. | B25H 3/021 |
| | | | | 206/363 |
| 6,527,123 B1 * | 3/2003 | Ausaf | ..................... | A47J 47/14 |
| | | | | 206/541 |
| 6,547,073 B1 * | 4/2003 | Lee | ................... | B65D 73/0014 |
| | | | | 206/378 |
| 6,632,189 B1 * | 10/2003 | Fallen | ................ | A61M 1/3664 |
| | | | | 206/363 |
| 6,915,901 B2 * | 7/2005 | Feinberg | .......... | A61B 17/00491 |
| | | | | 206/363 |
| 7,100,771 B2 * | 9/2006 | Massengale | .......... | A61M 5/002 |
| | | | | 206/363 |
| 2006/0086634 A1 * | 4/2006 | Steppe | .................. | A61B 50/30 |
| | | | | 206/438 |
| 2007/0045152 A1 | 3/2007 | Kwok et al. | | |
| 2008/0093246 A1 * | 4/2008 | Duchamp | ............. | B65D 5/307 |
| | | | | 206/438 |
| 2008/0185314 A1 * | 8/2008 | Tomasello | ............. | A61B 18/24 |
| | | | | 206/570 |
| 2010/0094192 A1 | 4/2010 | Peters et al. | | |
| 2011/0089072 A1 | 4/2011 | Gillam | | |

* cited by examiner

DISPOSABLE KIT FOR MEDICAL APPARATUS

CROSS REFERENCE TO RELATED APPLICATIONS

This application claims priority to European application EP 16165578.2 filed Apr. 15, 2016, the contents of such application being incorporated by reference herein.

FIELD OF THE INVENTION

The invention relates to pre-assembled disposable kit or packaging for a medical apparatus, and in particular concerns a pre-assembled disposable kit where at least one bloodline and/or at least one filter adapted to filtering fluid passing through the kit are fixed on a holder mountable to the medical apparatus.

BACKGROUND OF THE INVENTION

A known disposable packaging device includes a wall for accommodating a medical article for use in conjunction with a medical machine. The medical article includes mounting means, and the medical machine includes mounting means for engagement with the mounting means of the medical article. In the packaging device, a passage opening is defined in the wall and has a configuration such that the mounting means of the packaged article can be engaged with the mounting means of the machine.

Another known device resides in a mount for removable attachment thereof to a medical apparatus. The mount provides a hollow space for accommodating a medical device therein and comprises a first and a second side part that are elastically deformable so as to be compressed prior to the mounting thereof and to expand after having been inserted into corresponding mounting sections at the medical apparatus.

Known preassembled arrangements as mentioned above are arranged and packed in a way to protect tubes (lines, filters and components) during the lifetime of the product of storage and shipment until use. The product protection is currently obtained for instance through special boxes, pouches or customized thermoformed blister.

A main problem during the packaging of a complex kit is tube kinking especially of pump segments, and the pressure mark (markings caused by components pressed together). A known conventional packaging system as currently used cannot properly protect the packaged product because it is designed to protect external layers only, without taking into consideration that critical components of the products are located also in the interior of the package.

SUMMARY OF THE INVENTION

In view of the above, an object of the invention resides in providing a packaging configuration of a disposable kit for a medical apparatus arranged to protect also the interior areas of the product, and in particular to prevent tube kinking, especially of pump segments, and a pressure mark from occurring.

In addition, the invention shall provide a tray configuration permitting the product to be enveloped by the kit, and the kit to be packed in a way to protect interior components such as e.g. lines and filters during the entire lifetime of the product.

Moreover, the invention shall facilitate and accelerate the setup of a kit on a medical apparatus or machine.

According to aspects of the present invention, this object is accomplished by a disposable kit for a medical apparatus as defined in the independent claim. Advantageous further developments of the invention are subject of the accompanying dependent claims.

Thereby, a general idea underlying the present invention resides in creating and providing (besides an external pouch) a packaging configuration in preferably the form of a tray that is able to protect also the hidden/interior areas of the product, wherein the configuration of the tray is arranged so as to permit the kit to envelope it. Ideally, the packaging configuration is customized to correlate with, or fit, a disposable kit encompassing surgical, medical, dental and veterinary apparatus and instruments, such as e.g. hoses, filters, bags, adapters, valves sold as a unit, for the treatment or processing of human whole blood, especially for the treatment or processing of infusion solutions and body fluids, such as blood and the like.

More specifically, a special tray with some dedicated housings for the pump segments (blood, fluids, citrate and the like) and for the main drip chambers is provided. The housing is arranged to hold in place tubing and components through a cover designed to be removed during unpackaging of the kits. The tray is not a mere container but is formed to follow a geometry of a routing of kits to obtain a maximums protection. Moreover, the tray is arranged to work, or be applicable or mountable, from both of its sides. In a configuration as mentioned above, a first part of the kit or tray structure comprises a hinged section which is foldable around a second part of the kit or tray structure in a way that the set as a whole is folded on itself during the packaging thereof so as to encompass or enclose disposables placed in between.

As used herein, while the term "disposable kit" may designate the entire kit and tray structure as a whole, including disposables as the case may be, the term "kit" alone may designate the first part and the term "tray" alone may designate the second part, so that, in other words, a packaging configuration is provided wherein the tray is at least partially enclosed or encompassed by the kit and then put into kind of a bag, i.e. the packaging is customized so as to fit in a predetermined way with disposables in the disposable kit as a whole already upon packaging and to protect the disposables until the unpacking and use thereof. Upon unpacking the kit and tray, the hinged section of the kit may be unfolded in order to grant access to the disposables, the disposables may be put in place in a predetermined manner within the kit and tray structure, and the hinged section of the kit may be folded back again so as to hold and protect the disposables in place during the mounting of the kit structure to the medical apparatus and its use.

As regards materials and production processes, because in medical packaging security, tamper-resistance, safety and traceability are usually critical, for example thermoformed and/or plastic packaging can be tailored to be custom-made and used to adapt to and meet corresponding requirements. Materials in thermoforming may, in singular use or in combination, include PP (Polypropylene), PVC (Polyvinyl Chloride), PET (Polyethylene Terephthalate), PETG (Modified PET), Polyurethane, HIPS (high impact polystyrene), OPS (oriented polystyrene), HDPE (high-density polyethylene) and the like, without being limited thereto.

Advantageously, the disposable kit or kit and tray structure can be quickly and easily unpacked, and provides both a reliable and safe anti-kinking system for interior pump segments, drip chamber protection and the like.

More specifically, according to an aspect of the present invention, there is provided a disposable kit for a medical apparatus, comprising: a first subassembly arranged in substantially the form of a tray; and a second subassembly formed of a plurality of sections foldably connected to each other, wherein at least one of the plurality of sections is arranged to be hinged away onto the tray and thereby to enclose at least a region of the tray corresponding to a length of the section being hinged away. In this manner, the tray is advantageously surrounded by the second subassembly as a kit part, can in this configuration be packaged into a bag, and then be further packaged in greater number in a secondary package like e.g. a box. After shipment, the disposal kit can quickly be unpacked and also quickly be mounted to a machine or medical device or apparatus.

Preferably, the plurality of sections comprise at least a left section, a middle section and a right section, and wherein the left section and the middle section are foldably connected with a first hinge and the middle section and the right section are foldably connected with a second hinge such that each of the left section and the right section are arranged to be freely swingable with respect to the middle section. The partition into at least three sections or wings is advantageous in that the number of parts is overseeable while still providing sufficient flexibility. If two of the three parts are about the length of the tray, the third part can be folded around the tray from either side the tray is placed with respect to the second subassembly.

Preferably, the tray is configured as a substantially flat plate, said plate having protrusions extending to a predetermined height and forming a first elevated region on a first side of the tray and a second elevated region on a second side of the tray, and said first and second elevated regions being configured to have recesses forming channels in said first and second elevated regions. In this manner, a three-dimensional configuration of the tray can be provided which can be adapted to required tube section lengths and, placing the tube sections in the channels, provide protection from pressure acting on them.

Preferably, the left section of the second subassembly comprises first mounts arranged to hold ends of first tube sections such that bent regions of the first tube sections extend beyond an outer definition of the left section and correspond in form and/or length to the channels formed in one of the first and second elevated regions of the tray; and the right section of the second subassembly comprises second mounts arranged to hold ends of second tube sections such that bent regions of the second tube sections extend beyond an outer definition of the right section and correspond in form and/or length to the channels formed in the other one of the first and second elevated regions of the tray. Since the tube sections are intended to be accommodated and protected in the tray channels, the tube sections can advantageously be preconfigured and preinstalled on the second subassembly. In this manner, the packaging of the disposable kit is less prone to faults and unpacking is facilitated. Also, set-up time and time to operation are shortened after unpacking the kit.

Preferably, the tray is arranged to be placed on the second subassembly at a position in which the bent regions of one of the first and second tube sections substantially match with the corresponding channels in the tray facing these bent regions, and further arranged to then approach the second subassembly such that the bent regions matching with the corresponding channels in the tray are accommodated in said channels. Since the channels are predefined on then tray and the bent regions are dimensioned and pre-formed to substantially match with the channels, it is very easy to put the tray and the second subassembly together by simply aligning the tray channels with the bent regions and then sinking the bent regions into the channels.

Preferably, when the tray is placed on the second subassembly and the bent regions are accommodated in said channels, the one of the plurality of sections having the other one of the first and second tube sections is arranged to be hinged away via its hinge around an end of the tray remote from the channels accommodating the bent regions. When the bent tube regions at one foldable section are accommodated in their respective channels, bent tube regions at the remote foldable section (at the other end of the second subassembly) are exposed to the outside of the foldable section. Since the tray is about the length of two of the three sections, it ends sufficiently before the hinge and the foldable section including the exposed tube sections can be hinged away around the tray edge toward the back side of the tray.

Preferably, the tray comprises an accommodation structure and the second subassembly comprises a supporting protrusion formed to be accommodated in the accommodation structure; and the one of the plurality of sections is arranged to be hinged away to an extent that the supporting protrusion accommodates in the accommodation structure and at the same time the bent regions of the other one of the first and second tube sections substantially match with the corresponding channels in the tray facing these bent regions and are accommodated in said channels. The accommodation structure and support protrusion cooperate in a way that they provide a spacer abutting against the tray in a predetermined position and at the same time limiting the hinging angle of the section when swinging backwards. Thereby, the hinging angle is limited to a value at which the exposed tube sections of the swinging section safely accommodate in the channels on the back side of the tray. Advantageously, the accommodation structure and supporting protrusion configuration is provided as a snap-in configuration so that the supporting protrusion of the folding section can snap into the accommodation structure of the tray in a desired end position, preventing the folded section from unwantedly unfolding itself.

Preferably, at least one cover section is arranged to be mounted to the tray in at least one of the elevated regions to thereby cover the bent regions of the first and second tube sections accommodated in the channels. Since the channels are open in order to allow the tube sections to accommodate therein, covering them after placing the tube sections therein provides additional protection and safely holds them in place.

Preferably, at least one of the plurality of sections is arranged to mount at least one filter. Advantageously, one or more filters (or other components as need be) can be preinstalled and/or pre-connected with proper tubing in order to further facilitate the set-up of the kit and prevent set-up errors e.g. during connecting tubes. Pre-mounting filter and/or other components also ensures provision of suitable devices and prevents picking of wrong components during preparation/set-up of the kit.

Preferably, the tray and/or the second subassembly comprise spacers arranged to maintain a distance and to provide storage room for storage of installable disposals between the tray and the second subassembly in a hinged away state of the at least one of the plurality of sections. If the foldable sections are formed to be convex while the tray is formed to be substantially flat, cavities between the tray surface and that of the foldable sections can be utilized to store and pack, and deliver or transport, additional or optional disposals such as seals, connectors, tubes, containers and the like which are then equally protected by the hard-shell like configuration of at least the second subassembly from pressure being unwantedly exerted on them.

As used herein, the devices, structures, configurations and/or components constituting the disposable kit for a medical apparatus described and referred to herein may be configured to provide a variety of modifications, including more or less preinstalled configurations and/or separate parts to be put in proper place and connected upon unpacking the kit from a secondary package holding at least one kit, and preferably holding a plurality of kits, e.g. four kits packed separately in e.g. plastic bags or the like and setup of the kit for use.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

It is noted that similar or like parts visualized throughout the drawings and figures may be denoted by like reference numerals, and details thereof will not be described or explained redundantly. It is further noted that throughout the drawings and figures tubes and other components are omitted or hidden in order to provide an improved vision of the first and second subassemblies.

Figure 1:
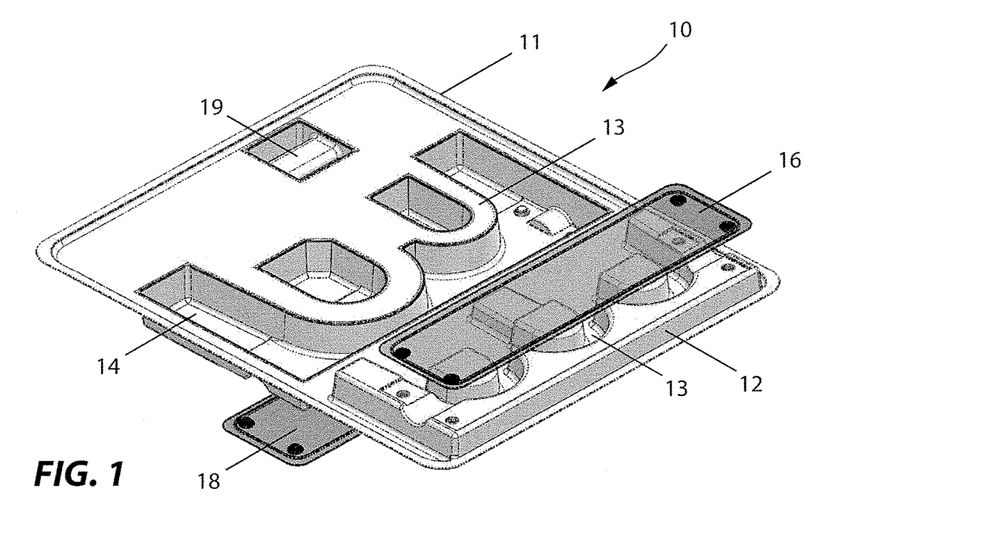
FIG. 1 shows a perspective view of a first subassembly or component group of a disposable kit for a medical apparatus according to a preferred embodiment of the invention, seen from a first side.
Figure 2:
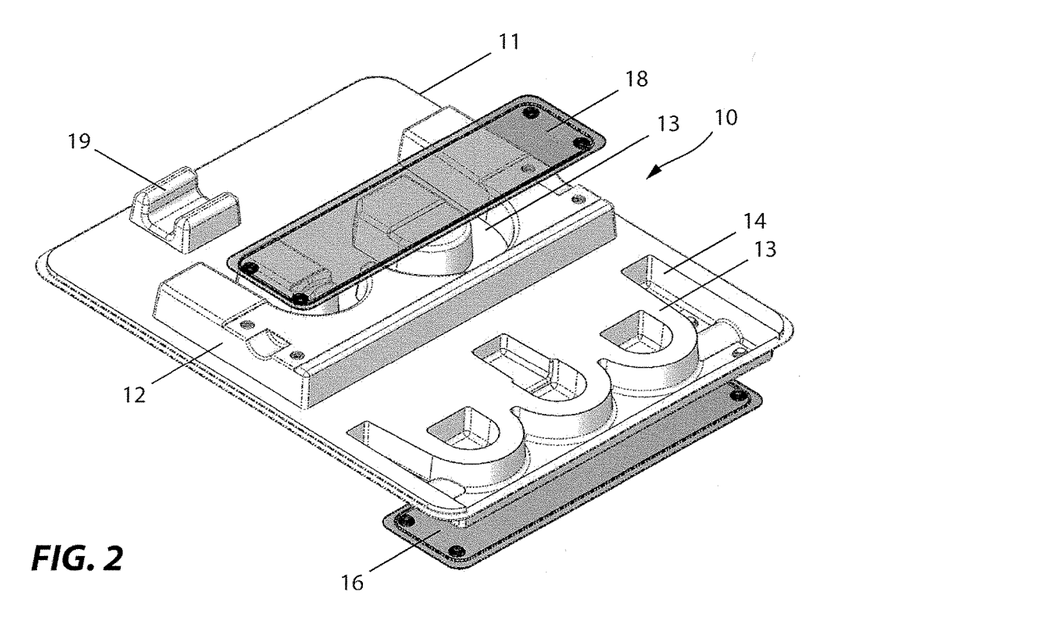
FIG. 2 shows a perspective view of the first subassembly seen from a second side opposite to the first side.

FIG. 1 shows a perspective view of a first subassembly 10, or component group, of a disposable kit for a medical apparatus according to a preferred embodiment of the invention, seen from a first side, e.g. from above, and FIG. 2 shows a perspective view of the first subassembly 10 seen from a second side opposite to the first side, e.g. from below (with the first subassembly 10 having e.g. been turned upside down). Hereinafter, the first subassembly 10 is also referred to as a tray of a disposable kit. In other words, FIGS. 1 and 2 show respective tray overviews.

In particular, the first subassembly 10 may comprise a preferably rectangular and substantially flat tray 11 having a number of recesses 12 and/or protrusions 14 formed to e.g. guide or follow disposals such as tubes, fluid lines, filters and the like required or foreseen for predetermined operation of the disposable kit when set up for operation and mounted to the medical apparatus. It is noted that the outer appearance of the tray 11, as a first part of a kit and/or tray structure forming the disposable kit as a whole, may have a form other than that of basically a rectangle as long as the form can suitably interact with a second subassembly as a kit part to be described later.

As also shown in FIG. 1 and FIG. 2, a predetermined number of covers, e.g. a first cover 16 and a second cover 18, may be provided and arranged to be mounted at predetermined positions, e.g. a first position and a second position, respectively, of the tray 11 so as to at least partially cover channels 13 formed by the protrusions 12 and/or recesses 14 in the tray 11. For example, the first position may be a position at an end section or portion of the tray 11, and the second position may be a position at a middle section or portion of the tray 11, without being limited thereto. In this preferred embodiment, the first and the second cover 16, 18 are preferably like parts of a rectangular form of approximately a length or a width of the tray 11 while being shorter in width or length than the tray 11 so that they extend over substantially the length or width of the tray 11 but only partially cover the tray area or surface in at least a channel region thereof. The first and second covers 16, 18 may be removably or fixedly fastened to the tray 11 by suitable means such as e.g. snap-in configurations, magnets, bonding pads or screws. Predetermined positions thereof on the tray 11 may be indicated by respective cutouts or recesses preformed into the tray 11. In addition, the first and second covers 16, 18 may be transparent, semi-transparent or opaque or non-transparent and made of the same material as that of the tray 11 or a different material. Neither of the aforementioned configurations and features of the first and second covers 16, 18 are limited to the aforementioned specific examples.

Figure 3:
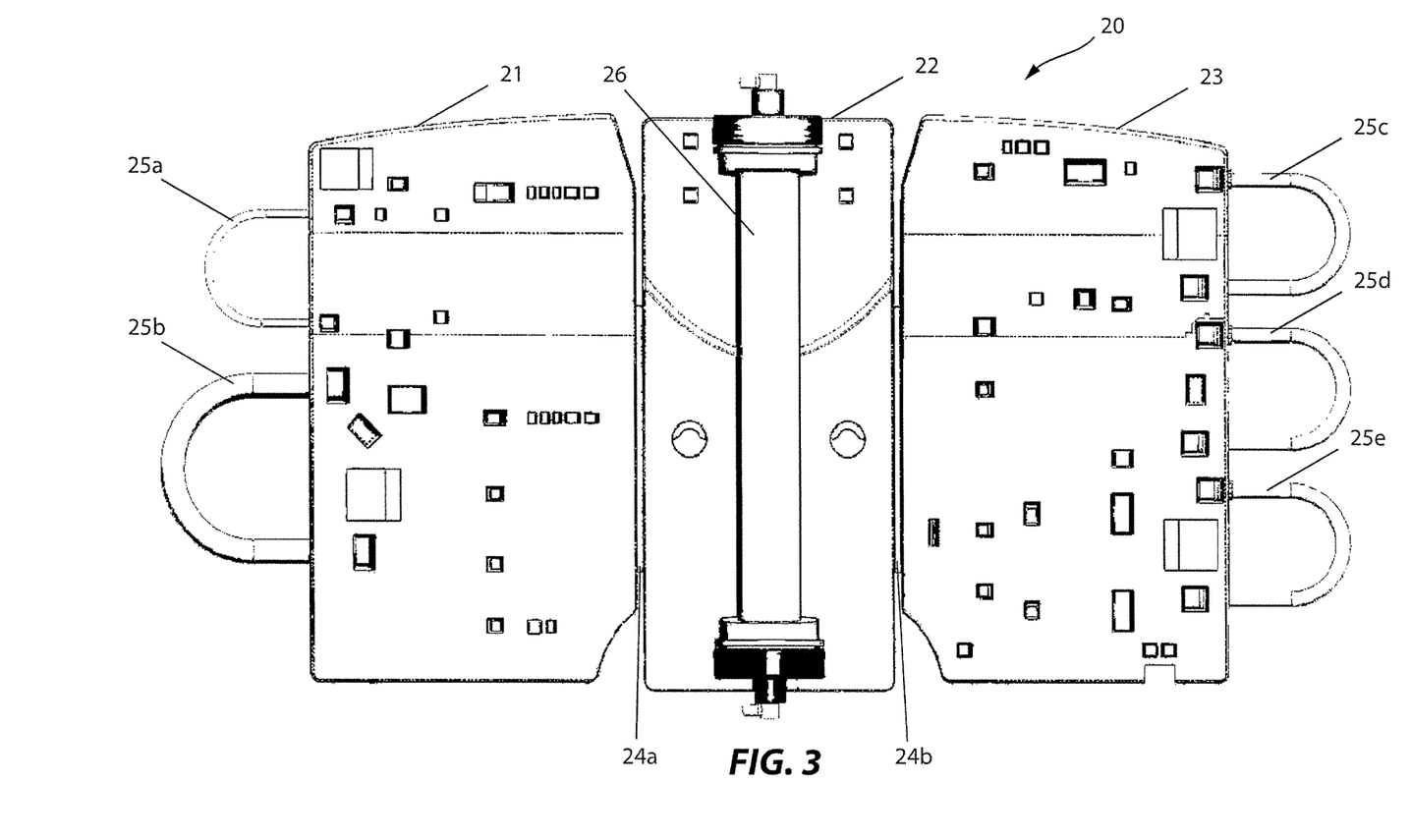
FIG. 3 shows a plan view of a second subassembly or component group of the disposable kit for a medical apparatus according to the embodiment, seen from a first side.
Figure 4:
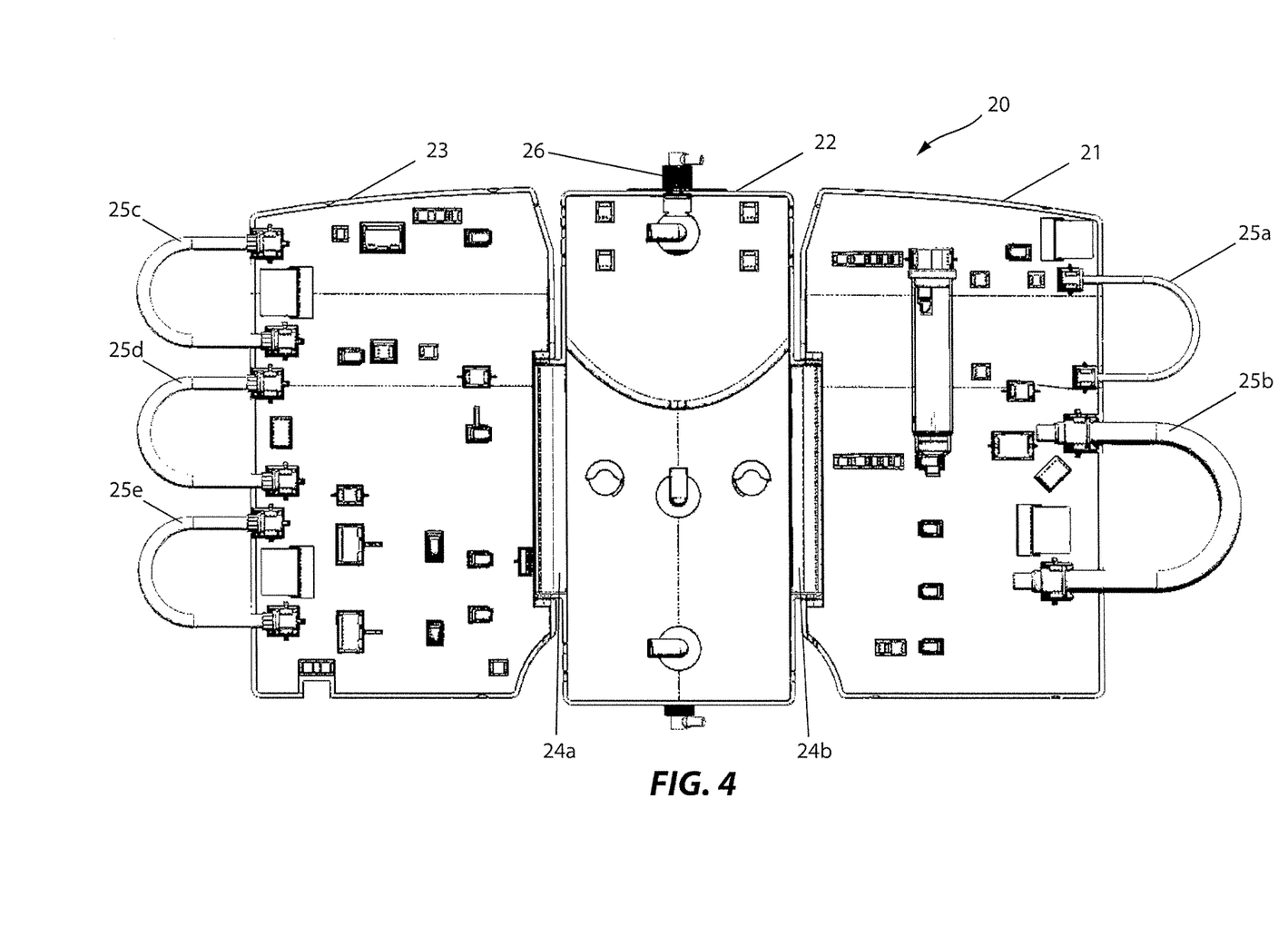
FIG. 4 shows a plan view of the second subassembly seen from a second side opposite to the first side.

FIG. 3 shows a plan view of a second subassembly or component group 20 of the disposable kit for a medical apparatus according to the embodiment, seen from a first side, e.g. a front side, and FIG. 4 shows a plan view of the second subassembly 20 seen from a second side opposite to the first side, e.g. a rear side (with the second subassembly 20 having been turned over). Hereinafter, the second subassembly 20 is also referred to as a kit or kit part of a disposable kit. In other words, FIG. 3 and FIG. 4 show a respective kit overview.

In particular, the second subassembly 20 may in the present embodiment consist of three parts, sections or wings, i.e. a left or first section 21, a middle or second section 22 and a right or third section 23 of a substantially rectangular form. The left section 21 and the right section 22 may be attached to the middle section 22 with hinges 24a, 24b, respectively, so that they can be hinged away with respect to the middle section 22 in a predetermined angle range. In other words, the combined structure of the second subassembly 20 may consist of a center part (the middle or second section 22) to which a first wing (the left or first section 21) and a second wing (the right or third section 23) may be movably, i.e. foldably, mounted with the hinges 24a, 24b, respectively. The predetermined angle range can be arranged to extend in a way that each of the left and right sections 21, 23 can fold themselves over or onto the middle section 22 and contact the same in a maximally hinged away position.

In the present embodiment, the middle section 22 may be formed to be smaller in areal extension than the left and right sections 21, 22 so that in the maximally hinged away position the left and right sections 21, 23 may overlap and cover the middle section 22 entirely. It is understood that both of the left and right sections 21, 23 can be hinged away in the same direction with respect to the middle section 22. In this case only one of the left and right sections 21, 23 overlays the middle section 22 in the maximally hinged away position, and the other of the left and right sections 21, 23 overlays the section overlaying the middle section 22. It is further understood that the left section 21 can be hinged away in one direction with respect to the middle section 22 and the right section 23 can be hinged away in the opposite direction with respect to the middle section 22. In this case only both of the left and right sections 21, 23 can overlay the middle section 22 in the maximally hinged away position.

In a state in which the left, middle and right sections 21 to 23 are mounted together, the resulting three-part subassembly 20 can be arranged to carry a predetermined number of preinstalled components such as tube sections 25a to 25e (preferably on the left and right sections 21, 23) and/or e.g. a filter 26 (preferably on the middle section 22). In the present embodiment, two tube sections 25a, 25b are exemplified to have different diameters and to be mounted to the left section 21 at an inlet and an outlet thereof, one filter 26 is exemplified to be mounted to the middle section 22, and three tube sections 25c to 25e of a same diameter are exemplified to be mounted to the right section 23. It is understood that actual numbers of preinstalled components are not limited to these exemplary numbers.

The filter 26 is not specifically limited to a particular kind of filter but can be arranged to be a filter having at least a fluid inlet and at least a fluid outlet and adapted to fluid(s) flowing in operation through the disposable kit.

The tube sections 25a to 25e are not specifically limited to the length, form, diameter and/or thickness configurations shown in the drawing, but can be any of length, form, diameter and/or thickness suiting the purpose and operation of the practical disposable kit. The preinstalled tube sections 25a to 25d may be configured to have respective open ends arranged to be respectively connected, using as such known connectors, seals, holders, clamps and the like, to further tube lines upon setup of the disposable kit for use and/or operation in order to form a predetermined fluid flow path for a fluid flowing through the disposable kit.

FIGS. 3 and 4 also illustrate a number of further constructional details formed into the left, middle and right sections 21 to 23 and placed distributedly over them, such as recesses, protrusions and through holes, which may serve as e.g. guides for tube lines in the set-up and operational state, as e.g. spacers to adapt to the tray 11 form and/or to prevent pressure from acting on tube lines passing underneath or nearby, and/or as e.g. mouldings purposefully enhancing the stiffness of the left, middle and right sections 21 to 23.

It is noted that the outer appearance of the left, middle and right sections 21 to 23 as a second part of the kit and/or tray structure may have a form other than that of basically a rectangle as long as the form can suitably interact with the tray 11 of the disposable kit to be described later. Also, the left, middle and right sections 21 to 23 may be of a transparent, semi-transparent or opaque, or non-transparent material the same or different than that of the tray 11 or the first and second cover 16, 18.

A more detailed description on one possible configuration of the second subassembly 20/disposable kit is given in US 2010/0094192 A, the disclosure of which is incorporated by reference.

In order to prepare for packaging and transport, the first subassembly 10 (i.e. the tray 11) and the second subassembly 20 (i.e. the kit consisting of the first, second and third or left, middle and right sections or wings 21 to 23) are aligned with each other in a predetermined manner while still being kept separately.

Figure 5:
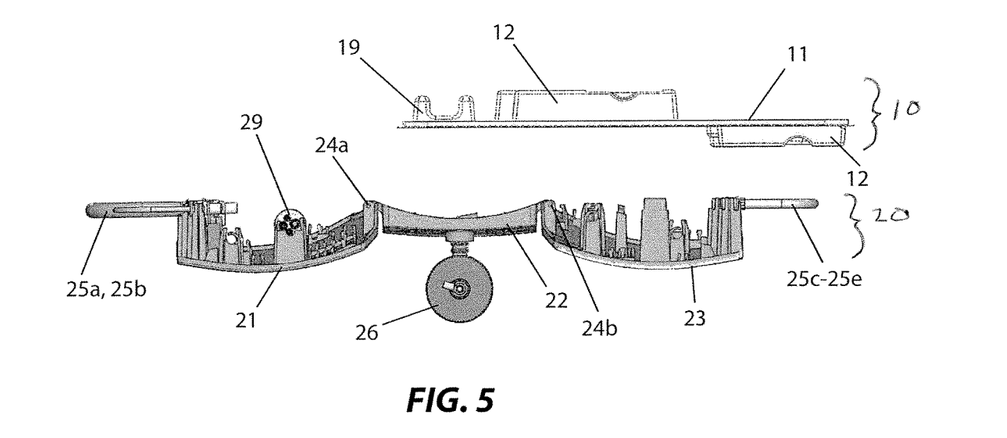
FIG. 5 shows a top view of the first and second subassembly held separately and aligned with each other in a mounting position.
Figure 6:
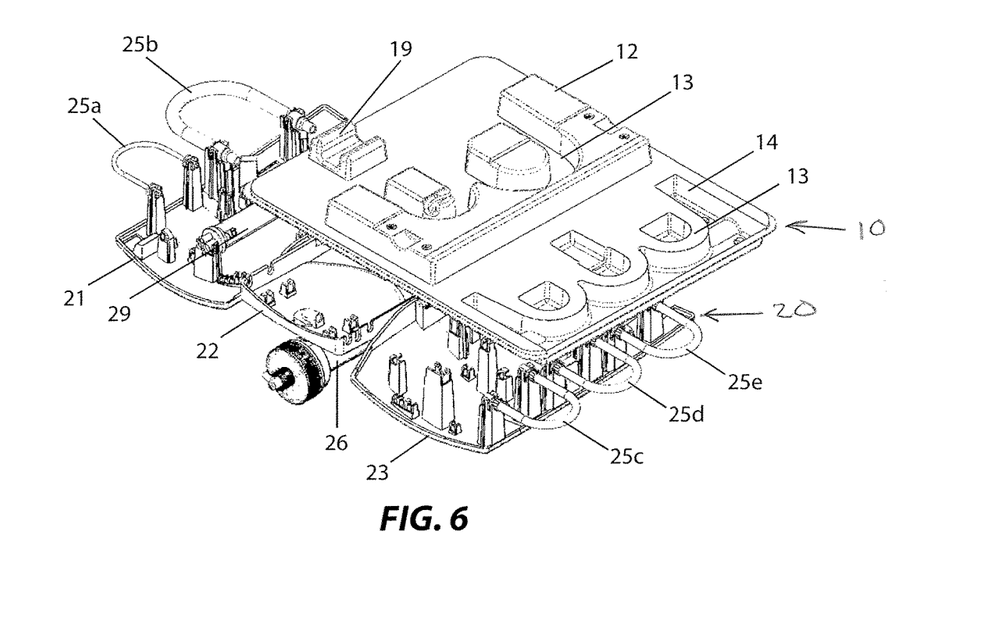
FIG. 6 shows a perspective view of the first and second subassembly held separately and aligned with each other in a mounting position.

FIG. 5 shows a top view of the first and second subassembly 10, 20 held separately and aligned with each other in a mounting position, and FIG. 6 shows a perspective view of the first and second subassembly 10, 20 laid one on another and/or attached to each other in the mounting position. As illustrated in FIG. 5 and FIG. 6, the tray 11 may be positioned over the second subassembly 20 so that locations or positions of recesses in the tray 11 correspond to locations or positions of the tube sections 25a, 25b of the left section 21 or the tube sections 25c to 25e of the right section 23.

In the present embodiment, the tray 11 is shorter in longitudinal extension by approximately the length of one section 21, 23 plus the length of one of the hinges 24a, 24b of the second subassembly 20.

That is, when the locations or positions of the recesses in the tray 11 are aligned with the locations or positions of the tube sections 25a to 25e of one of the left section 21 or the right section 23, the other end of the tray 11 is still sufficiently within the middle section 22, and the respective hinge 24a, 24b and left or right section 21, 23 close to that other end of the tray 11 are not prevented from being moved or hinged away with respect to the tray 11.

Referring back to FIGS. 1 and 2, the tray 11 may preferably be arranged as a substantially flat plate with protrusions 12 on one side of the plate and protrusions 14 on the other side of the plate. The protrusions on one side may form respective recesses on the other side and are formed such that channels 13 corresponding to a possible layout of the tube sections 25a to 25e are configured between the protrusions so that the tube sections 25a to 25e can be accommodated in the channels 13 in an assembled or mounted state of the disposable kit.

The tray 11 configured as above can thus be applied to the second subassembly 20 from either side.

For example, when the tray 11 is aligned with the tube sections 25c to 25e of the right section 23, as shown in FIG. 5 and FIG. 6, the corresponding protrusions 12/recesses 14 and channels 13 on the respective side of the tray 11 and the tube sections 25c to 25e face each other, and the protrusions 12/recesses 14 and channels 13 corresponding to the tube sections 25a and 25b are located on the other side of the tray 11 facing away from the second subassembly 20. In this alignment and orientation, the tray 11 extends longitudinally toward the first hinge 24a and ends inwards ahead of the first hinge 24a, i.e. does not extend over or beyond the first hinge 24a.

Alternatively, when the tray 11 is aligned with the tube sections 25a, 25b of the left section 21, the corresponding protrusions 12/recesses 14 and channels 13 on the respective side of the tray 11 and the tube sections 25a, 25b face each other, and the protrusions 12/recesses 14 and channels 13 corresponding to the tube sections 25c to 25e are located on the other side of the tray 11 facing away from the second subassembly 20. In this alignment and orientation, the tray 11 extends longitudinally toward the second hinge 24b and ends inwards ahead of the first hinge 24b, i.e. does not extend over or beyond the first hinge 24b.

Figure 7:
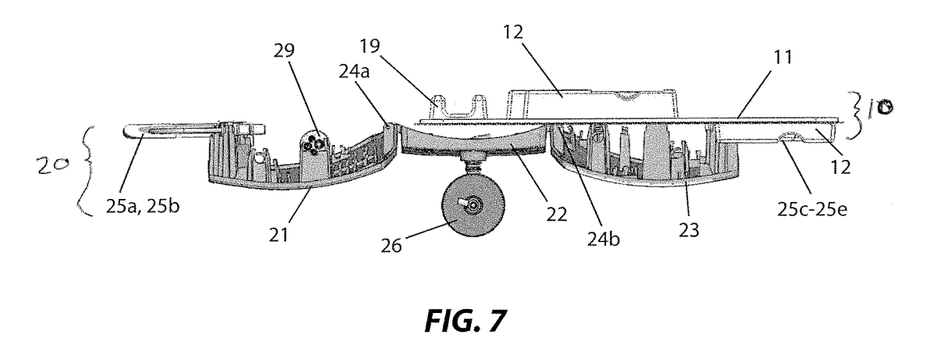
FIG. 7 shows a top view of the first and second subassembly laid one on another and/or attached to each other in the mounting position.
Figure 8:
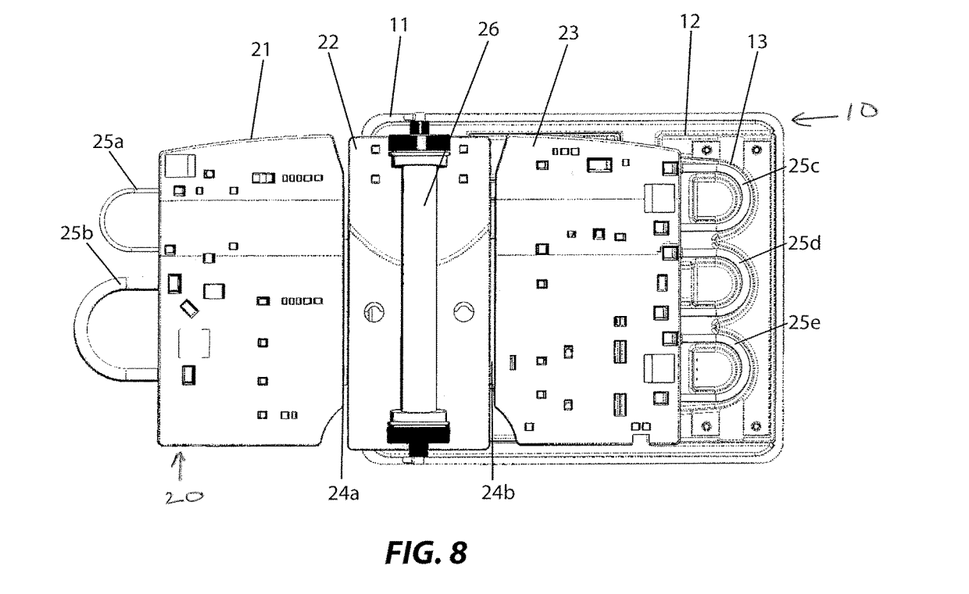
FIG. 8 shows a plan view of the first and second subassembly laid one on another and/or attached to each other in the mounting position.

FIG. 7 shows a top view of the first and second subassembly 10, 20 laid one on another and/or attached to each other in the mounting position, and FIG. 8 shows a plan view of the first and second subassembly 10, 20 laid one on another and/or attached to each other in the mounting position.

The view in FIG. 7 and FIG. 8 is basically the same as that of FIG. 5 and FIG. 6 except that the tray 11 has been lowered vertically and laid onto the second subassembly 20 so that the tube sections, in FIG. 7 and FIG. 8 the tube sections 25c to 25e, previously aligned with the facing channels 13 in the tray 11 are now accommodated in these channels 13, as best seen in FIG. 8. It is understood that because the tray 11 ends inwards and ahead of the first hinge 24a, the left section 21 can swing freely around the hinge 24a. In the present embodiment, the tray 11 and the second subassembly 20 may be removably fixed to each other by e.g. snap-in fasteners or clamps (not explicitly shown). For preparational and/or packaging purposes, it may however be sufficient to simply bring the tray 11 and the second subassembly 20 close to each other without connecting them physically via specific fasteners.

Figure 9:
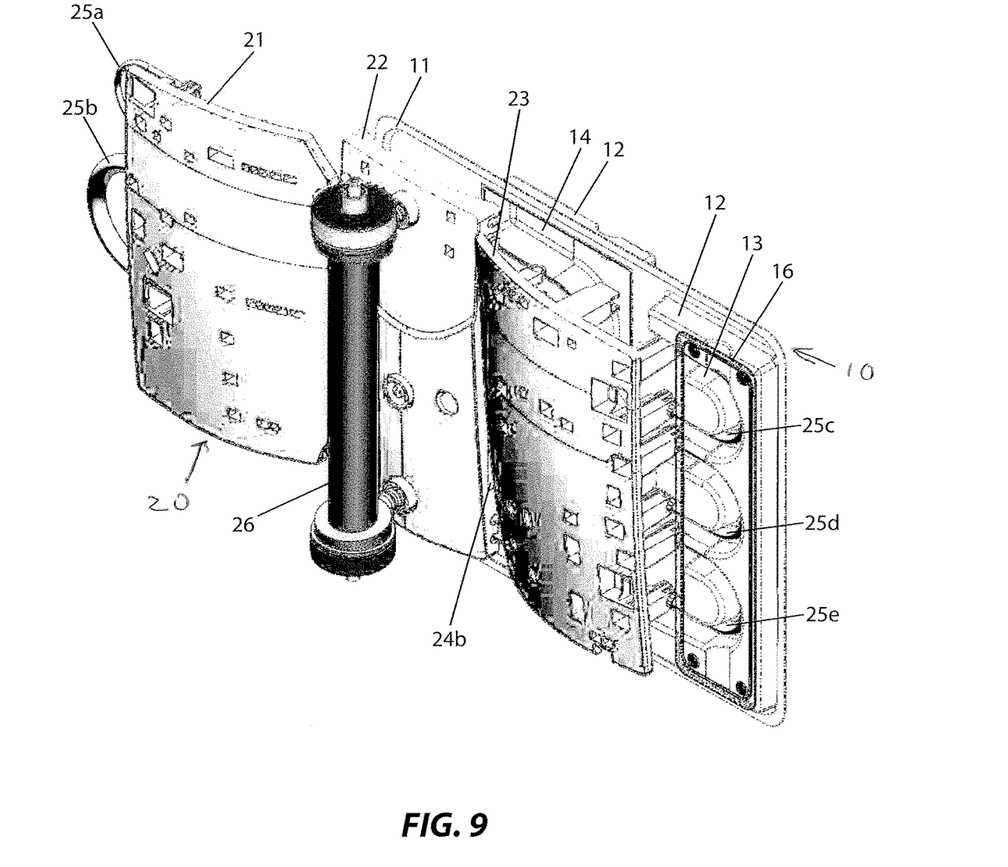
FIG. 9 shows a perspective view of the first and second subassembly with a first cover piece mounted to an end portion of the first subassembly.

FIG. 9 shows a perspective view of the first and second subassembly 10, 20 with the first cover piece 16 mounted to the end portion of the first subassembly 10, i.e. where the tube sections 25c to 25e are accommodated in the channels 13 formed by the protrusions 12 of the tray 11. As shown in FIG. 9, the mounting position of the first cover piece 16 may be such that it covers the tube sections 25c to 25e accommodated in the channels 13 formed by the protrusions 12 of the tray 11.

Figure 10:
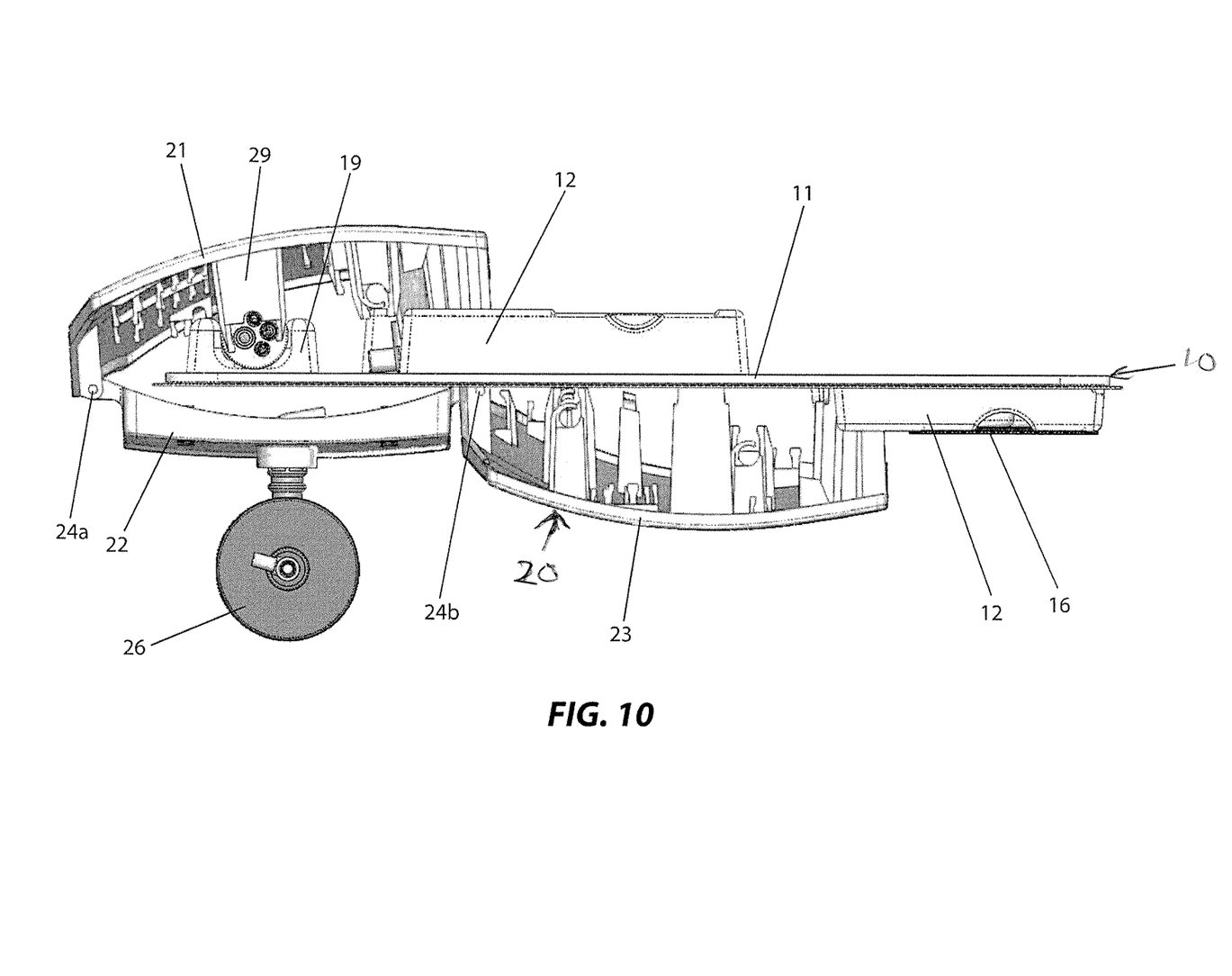
FIG. 10 shows a top view of the first and second subassembly a hinged section of the second subassembly folded toward and around a second end of the first subassembly.

FIG. 10 shows a top view of the first and second subassembly 10, 20. After the hinged section, i.e. the left section 21, of the second subassembly 20 is folded toward the end portion of the first subassembly 10, i.e. the tray 11, the left section 21 at the hinged section is folded around the hinge 24a toward the back side of the tray 11. Thereby, the left section 21 swings around the other or second end of the tray, approaching the free tube sections 25a and 25b toward the back side of the tray 11. In a final position, the left section 21 of the second subassembly 20 is swung or folded around the other end or end portion of the first subassembly 10, i.e. the tray 11.

As illustrated in FIG. 10, in the final position of the left section 21 at the hinged section, the left section 21 at least partially encloses or encompasses the tray 11, a protruding part 29 on the rear side of the left section 21 becomes accommodated in an accommodation structure or protrusion 19 of the tray 11, which may be formed into e.g. a tub-shape or a U-form, thereby physically supporting and stabilizing the left section 21 on the back side of the tray 11, and the tube sections 25a and 25b become accommodated in the tray 11 rear or back side channels 13 formed by the tray back side protrusions 12. Because of the support rendered by the protruding part 29, components such as disposals or the like placed in spaces or cavities between the left section 21 and the tray 11, and also the tube sections 25a and 25b are prevented from being pressurized so that pressure marks thereon can be safely prevented.

Figure 11:
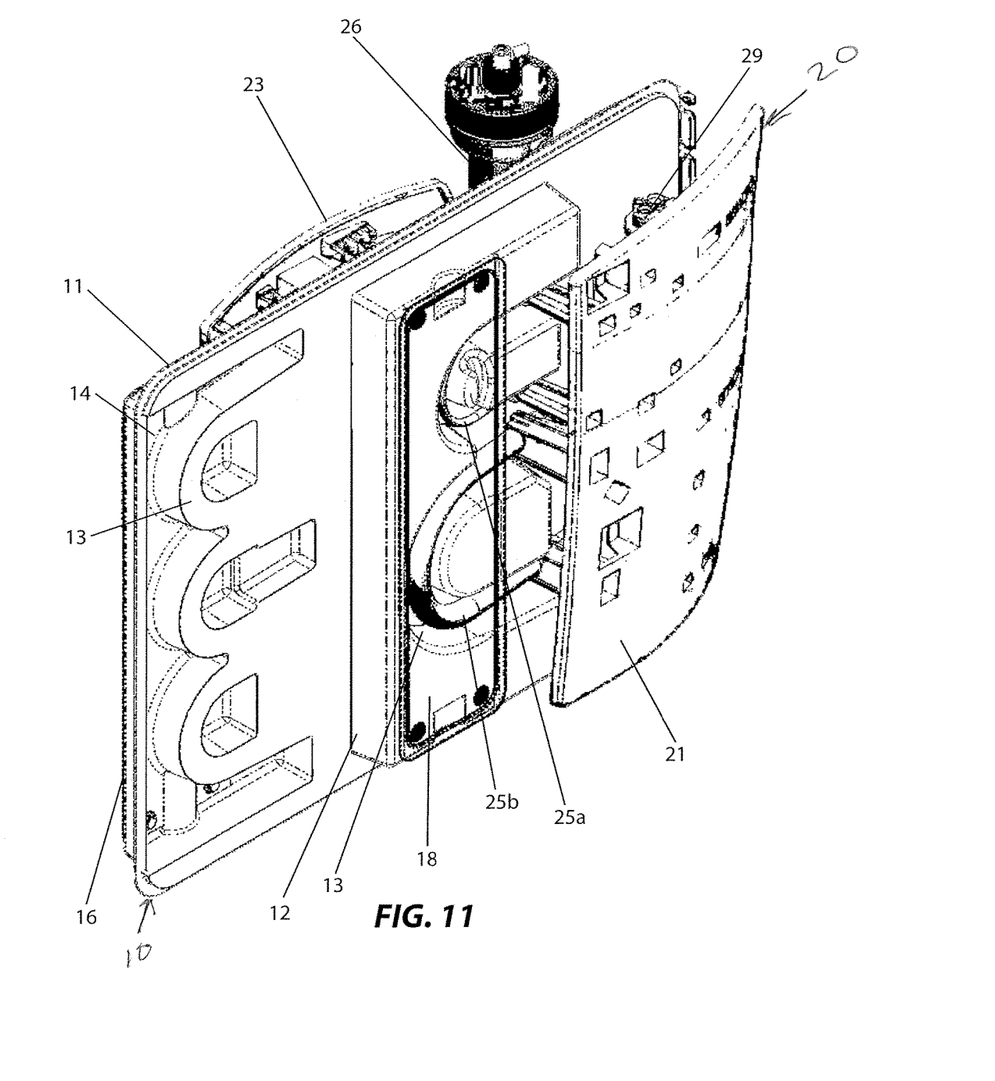
FIG. 11 shows a perspective view of the first and second subassembly in a final mounting and/or packaging state and with a second cover piece mounted to the middle section or portion of the first subassembly.

FIG. 11 shows a perspective view of the first and second subassembly 10, 20 with the second cover piece 18 mounted to the middle section or portion of the tray 11.

As can be seen in FIG. 11, the tube sections 25a and 25b are accommodated in the channels 13 formed by the protrusions 12 of the tray 11, and the hard-shell left section 21 protectively covers the open ends and connectors of the tube sections 25a and 25b.

As further illustrated in FIG. 11, in the final packaging state, the overall dimensions of the disposable kit including the first and second subassemblies 10, 20 are determined essentially by the length and the width of the tray 11 with the second subassembly folded onto itself and around one side or end of the tray 11. The free tube sections 25a to 25e held by or provided in the second subassembly 20 are safely accommodated in channels 13 formed by the protrusions 12 of the tray 11. The layout of the channels 13 can resemble the form of the tube sections 25a to 25e so that the channels 13 can follow the form of the tube sections 25a to 25e. Spacers support the hard-shell like wings, or sections 21 to 23 of the second subassembly 20 against the tray 11 so that any components mounted or loosely packed in space provided in between are safeguarded against pressure acting on them. The covers 16 and 18 fixedly mounted to the tray 11 prevent the tube sections 25a to 25e from exiting the channels 13 and from damage. A transparent configuration of the covers 16, 18 may allow visual observation and confirmation of the presence of the tube sections 25a to 25e also in the packaged state. The disposal kit arranged as above may be placed as a whole in a bag, which can be made of plastics and/or be sterile, removed from the bag without any pieces falling off or apart, and converted to larger quantities thereof for shipment using a secondary package or packet. Unpacking and mounting to a destination medical apparatus can be quick and easy by opening the secondary package or packet, taking out a disposable kit from its bag and unfolding it for further or supplementary operational setup. Snap-in fasteners may support tool-free handling and mounting.

As has been described above, a disposable kit for a medicarapparatus comprises a tray 11 and a subassembly 20 with a plurality of sections 21 to 23 foldably connected to each other. At least one of the sections 21 to 23 can fold itself onto the tray 11 so that the subassembly 20 encloses a region of the tray 11. When the tray 11 is laid on the subassembly 20 in a predetermined position, elevated channel regions formed on a front side of the tray 11 and facing the subassembly 20 can accommodate component installations of the subassembly 20, and a section of the plurality of sections 21 to 23 can be folded or hinged away to the rear side of the tray 11 so that component installations on that section can be accommodated in elevated channel regions formed on the rear side of the tray 11. In this manner, the subassembly 20 can form a hard-shell that at least partially surrounds the tray 11 and protects pre-installed or packed pressure-sensitive components, parts and or regions of the disposable kit.

Although specific amounts such as weight, absolute length, width and thickness, coloring, form and minor details of an overall disposable kit are not shown, such specifications are within the purview of the invention described hereinabove as will be understood to those skilled in the art. It is also to be understood that the specific text, sequence and content of configurations and components shown in the drawing and described herein are by way of illustration and example only and the apparatus, system and operation thereof are not to be limited thereby.

Therefore and as understood, the invention is not limited to the described preferred embodiment and modifications thereof, and combinations of at least parts of the embodiment, modifications and equivalents all within the scope defined by the appended claims may occur to the skilled person.

The invention claimed is:

1. A disposable kit for a medical apparatus, comprising:
a first subassembly arranged in the form of a tray having a first side and a second side, wherein the tray is configured as a plate having protrusions extending from the first side and the second side to predetermined heights and forming a first elevated region on the first side of the tray and a second elevated region on the second side of the tray, and wherein the first elevated region and the second elevated region each have one or more recesses forming channels; and
a second subassembly comprising:
   a plurality of sections foldably connected to each other, the plurality of sections including at least a left section and a right section; and
   one or more tube sections; and wherein
      the left section of the second subassembly comprises first mounts arranged to hold ends of one or more first tube sections such that bent regions of the one or more first tube sections extend beyond an outer definition of the left section and correspond in form to the channels formed in one of the first or second elevated regions of the tray;
      the right section of the second subassembly comprises second mounts arranged to hold ends of one or more second tube sections such that bent regions of the one or more second tube sections extend beyond an outer definition of the right section and correspond in form to the channels formed in the other one of the first and second elevated regions of the tray; and
      at least one of the plurality of sections is arranged to be folded onto one of the first side or the second side of the tray and thereby to enclose at least one of the channels of the tray.

2. The disposable kit for a medical apparatus according to claim 1, wherein the plurality of sections further comprises a middle section, and wherein the left section and the middle section are foldably connected by means of a first hinge and the middle section and the right section are foldably connected by means of a second hinge such that each of the left section and the right section are arranged to swing with respect to the middle section.

3. The disposable kit for a medical apparatus according to claim 1, wherein the tray is arranged to be placed on the second subassembly at a position in which the bent regions of one of the first tube sections and the second tube sections substantially match with the corresponding channels in the tray facing these bent regions, and further arranged to then receive the second subassembly such that the bent regions matching with the corresponding channels in the tray are accommodated in said channels.

4. The disposable kit for a medical apparatus according to claim 3, wherein when the tray is placed on the second subassembly and the bent regions are accommodated in said channels, the one of the plurality of sections having the other one of the first and second tube sections is arranged to be folded around an end of the tray remote from the channels accommodating the bent regions.

5. The disposable kit for a medical apparatus according to claim 1, wherein:
the tray comprises an accommodation structure and the second subassembly comprises a supporting protrusion formed to be accommodated in the accommodation structure; and
the one of the plurality of sections is arranged to be folded to an extent that the supporting protrusion accommodates in the accommodation structure and at the same time the bent regions of the other one of the first and second tube sections substantially match with the corresponding channels in the tray facing these bent regions and are accommodated in said channels.

6. The disposable kit for a medical apparatus according to claim 3, wherein at least one cover section is arranged to be mounted to the tray in at least one of the elevated regions to thereby cover the bent regions of the first and second tube sections accommodated in the channels.

7. The disposable kit for a medical apparatus according to claim 5, wherein at least one cover section is arranged to be mounted to the tray in at least one of the elevated regions to thereby cover the bent regions of the first and second tube sections accommodated in the channels.

8. The disposable kit for a medical device according to claim 1, wherein at least one filter is mounted to at least one of the plurality of sections.

9. The disposable kit for a medical device according to claim 1, wherein at least one of the plurality of sections is arranged to mount at least one filter.

10. The disposable kit for a medical device according to claim 5, wherein at least one of the plurality of sections is arranged to mount at least one filter.

11. The disposable kit for a medical device according to claim 1, wherein at least one of the tray or the second subassembly comprise spacers arranged to maintain a distance and to provide storage room for storage of installable disposals between the tray and the second subassembly in a folded state of the at least one of the plurality of sections.

12. The disposable kit for a medical device according to claim 5, wherein at least one of the tray or the second subassembly comprise spacers arranged to maintain a distance and to provide storage room for storage of installable disposals between the tray and the second subassembly in a folded state of the at least one of the plurality of sections.

13. The disposable kit for a medical device according to claim 8, wherein at least one of the tray or the second subassembly comprise spacers arranged to maintain a distance and to provide storage room for storage of installable disposals between the tray and the second subassembly in a folded state of the at least one of the plurality of sections.

* * * * *